United States Patent
Raab

(10) Patent No.: US 7,399,875 B2
(45) Date of Patent: Jul. 15, 2008

(54) FLUOROSILANE CONDENSATION PRODUCTS, THEIR PREPARATION AND USE FOR SURFACE MODIFICATION

(75) Inventor: Klaus Raab, Burgkirchen (DE)

(73) Assignee: Clariant Produkte (Deutschland) GmbH, Sulzbach (DE)

(*) Notice: Subject to any disclaimer, the term of this patent is extended or adjusted under 35 U.S.C. 154(b) by 342 days.

(21) Appl. No.: 11/286,526

(22) Filed: Nov. 23, 2005

(65) Prior Publication Data

US 2006/0111581 A1 May 25, 2006

(30) Foreign Application Priority Data

Nov. 23, 2004 (DE) .................. 10 2004 056 395

(51) Int. Cl.
*C07F 7/08* (2006.01)
*D06N 7/04* (2006.01)

(52) U.S. Cl. ............................. 556/479; 428/141

(58) Field of Classification Search ............... None
See application file for complete search history.

(56) References Cited

U.S. PATENT DOCUMENTS

| | | | |
|---|---|---|---|
| 3,243,409 A | 3/1966 | Kornicker |
| 3,422,060 A | 1/1969 | Fink |
| 3,465,020 A | 9/1969 | Frye |
| 3,677,977 A | 7/1972 | Bush |
| 5,442,011 A | 8/1995 | Halling |
| 5,800,926 A | 9/1998 | Nogami |
| 5,869,728 A | 2/1999 | Jenker |
| 6,255,516 B1 | 7/2001 | Jenker |
| 6,361,871 B1 | 3/2002 | Jenkner |
| 6,469,120 B1 | 10/2002 | Elfersy |
| 2002/0132952 A1 | 9/2002 | Miyadai |

FOREIGN PATENT DOCUMENTS

| | | |
|---|---|---|
| EP | 0838467 | 4/2003 |
| FR | 1145324 | 10/1957 |
| GB | 1267224 | 3/1972 |
| WO | WO 2004/096914 | 11/2004 |

OTHER PUBLICATIONS

Voronkov, MG, Collect, Czech. Chem. Commun., vol. 42, 1977, pp. 480-483 (Beilstein Online—XP002374102).
Voronkov, MG, et al., Pharm.Chem.J.(English Transl.); EN; 18: 1984, pp. 467-471 (Russia) (Beilstein Online—XP002374103).
Voronkov, MG, et al., J.Gen.Chem.USSR(English Transl. );EN;48;1978; pp. 2033-2038 (Beilstein Online—XP-002374104).
EPO Search Report and Office Action in connection with EP 05 024 040.7, Apr. 7, 2006.
English Language Abstract of WO 2004/096914, Nov. 11, 2004.
English Language Abstract of JP 50097616, Aug. 2, 1975.
English Language Abstract of JP 1189597, Jul. 13, 1999.
English Language Abstract of JP 09169779, Jun. 30, 1997.
English Language Abstract of JP 11189599, Jul. 13, 1999.
English Language Abstract of JP 10167767, Jun. 23, 1998.
JL Speier, Homogeneous Catalysis of Hydrosilation by Transition Metals, Adv in Organomettalic Chem, vol. 17, (1979), pp. 407-446.
MA Brooks, "A New Glycol-Silicon Polymer", J Polymer Sci, Part C, Polym Lett, (1989), vol. 27, No. 7.(German Abstract).
German Office Action, Application 102004056395.0, Jul. 4, 2005.

*Primary Examiner*—Samuel A Barts
(74) *Attorney, Agent, or Firm*—Richard P. Silverman

(57) ABSTRACT

The invention provides compounds preparable by the reaction of fluorous silanes (A)

$$R_F\text{—CH}_2\text{—CH}_2\text{—SiX}_3 \qquad (A)$$

where
$R_F$ is a fully or partially fluorinated alkyl radical,
X is Cl or O—$C_nH_{2n+1}$, and
n is an integer from 1 to 20, with one or more alcohols of the formula (B)

$$R(OH)_m(NH_2)_p \qquad (B)$$

where
R is a C— and H-containing organic radical and m and p are subject either to condition
a) $m \geq 2$ and $p=0$, or condition
b) $m \geq 1$ and $p \geq 1$.

15 Claims, No Drawings

FLUOROSILANE CONDENSATION PRODUCTS, THEIR PREPARATION AND USE FOR SURFACE MODIFICATION

The present invention relates to novel fluorosilane condensation products, to a process for preparing them and to their use. These condensation products of the present invention are preparable by condensation of fluorous silanes and multiply functionalized alcohols.

Fluorosilanes of the type

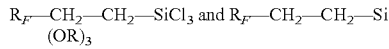
$R_F$—$CH_2$—$CH_2$—$SiCl_3$ and $R_F$—$CH_2$—$CH_2$—$Si(OR)_3$ where $R_F$=fluorinated alkyl, such as $C_nF_{2n+1}$
R=alkyl, such as $C_nH_{2n+1}$ are well known and can be prepared by hydrosilylation of $R_F$—CH=$CH_2$ with $HSiCl_3$ or $HSi(OR)_3$. The compounds of the $R_F$—$CH_2$—$CH_2$—$Si(OR)_3$ type can also be prepared by alcoholysis of $R_F$—$CH_2$—$CH_2$—$SiCl_3$ with monohydric alcohols R—OH.

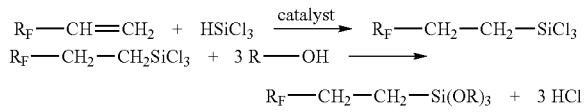
$R_F$—CH=$CH_2$ + $HSiCl_3$ $\xrightarrow{catalyst}$ $R_F$—$CH_2$—$CH_2$—$SiCl_3$
$R_F$—$CH_2$—$CH_2SiCl_3$ + 3 R—OH ⟶ $R_F$—$CH_2$—$CH_2$—$Si(OR)_3$ + 3 HCl JP-50 097 616 describes the $H_2PtCl_6$-catalyzed hydrosilylation of $C_6F_{13}$—CH=$CH_2$ and $HSiCl_3$ and also the subsequent reaction with ethanol to form

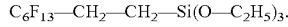
$C_6F_{13}$—$CH_2$—$CH_2$—$Si(O$—$C_2H_5)_3$.

JP-11 189 597 and EP-838 467 disclose analogous Pt(0)-catalyzed hydrosilylations.

JP-09 169 779 and JP-11 189 599 describe alcoholysis reactions of $R_F$—$CH_2$—$CH_2$—$SiCl_3$ with monohydric alcohols and JP-10 167 767 describes the alcoholysis product with ether alcohols such as methyldiglycol.

A general overview of hydrosilylation products and derivatization chemistry is given for example by J. L. Speier, Advances in Organometallic Chemistry, Vol. 17 (1979), 407.

The present invention has for its object to provide high-performance coating materials for the hydrophobic/oleophobic finishing of surfaces. These coating materials shall be sufficiently water-soluble for waterborne application, and they shall ideally not be volatile compounds.

It has now been found that this object is achieved, surprisingly, by compounds which are oligomeric or polymeric fluorosilane condensation products and hereinafter also simply referred to as condensation products, which are preparable by a condensation reaction or polycondensation reaction of at least two reactants (A) and (B).

The invention accordingly provides compounds preparable by the reaction of fluorous silanes (A)

$R_F$—$CH_2$—$CH_2$—$SiX_3$     (A)

where $R_F$ is a fully or partially fluorinated alkyl radical,
X is Cl or O—$C_nH_{2n+1}$, and
n is an integer from 1 to 20, with one or more alcohols of the formula (B)

$R(OH)_m(NH_2)_p$     (B)

where
R is a C— and H-containing organic radical and m and p are subject either to condition
a) m≧2 and p=0, or condition
b) m≧1 and p≧1.

The invention further provides a process for preparing the compounds of the present invention by reacting fluorous silanes of the formula (A) with alcohols of the formula (B).

The invention further provides formulations comprising at least one of the compounds of the present invention and one or more further components selected from the groups
(a) solvents, in particular alcohols, more preferably isopropanol
(b) water
(c) neutral, anionic, cationic or amphoteric surfactants
(d) alkoxysilanes, in particular tetraethoxysilane
(e) acids
(f) bases.

The invention further provides for the use of the compounds according to the present invention or of the above-described formulations for modifying the properties of surfaces and small particles.

The present invention further provides for the use of the compounds according to the present invention and of the above-described formulations for hydrophobicizing and oleophobicizing surfaces composed of glass, ceramic, mineral building materials, lacquers, metal, plastic, wood, paper or textile fabrics and also of small particles.

The present invention further provides a process for modifying the properties of surfaces and small particles by applying the compounds of the present invention or the above-described formulations to these.

The present invention further provides a process for hydrophobicizing and oleophobicizing surfaces composed of glass, ceramic, mineral building materials, lacquers, metal, plastic, wood, paper or textile fabrics and also of small particles by applying the compounds of the present invention or the above-described formulations to these.

When (A) and (B) are condensed or polycondensed, HX is detached. When a very large molar excess of (B) is used, in which case it is preferable to meter (A) to an initial charge of (B), the products are mainly monomers of the formula (A)(B)$_3$ in a mixture with excess (B). Oligomers and polymers having increasing molar masses are formed in ever larger proportions when the molar ratio of the reactive groups in (A) and of the reactive groups in (B) is adjusted ever closer to the exact stoichiometric ratio. When (B) comprises amino groups and fluorous silanes (A) where X=Cl are used, the condensation products of the invention will also comprise ammonium groups with chloride Cl$^-$ as counter-ions. The oligomeric and polymeric condensation products may have a linear, cyclic, branched or crosslinked construction. The structure and the properties of the condensation products can be influenced through the choice of (A) and (B), the number of reactive groups in (B), the mixing ratio of (A) to (B), the form of metering, mixing and order of addition of (A) to (B), of (B) to (A) or of (A) and (B) simultaneously and also the degree of removal of the detached HX from the condensation product.

In one preferred embodiment, n is an integer from 1 to 4 when X=O—$C_nH_{2n+1}$ in the formula (A) for the fluorous silanes.

In one preferred embodiment, $R_F$ is a perfluoroalkyl radical having 1 to 24, in particular 2 to 16 and specifically 3 to 6 carbon atoms. In another preferred embodiment, $R_F$ is a radical of the formula (1)

$$R_F'\text{---}(CH_2\text{---}CF_2)_b\text{---} \tag{1}$$

where $R_F'$ is a perfluoroalkyl group having 1 to 16 and in particular 2 to 6 carbon atoms and b is an integer from 1 to 12.

In another preferred embodiment, $R_F$ is a radical of the formula (2)

$$F\text{---}(CF_2\text{---}CF_2)_d\text{---} \tag{2}$$

where d is an integer from 1 to 12.

The alcohols of the formula (B)

$$R(OH)_m(NH_2)_p \tag{B}$$

can be selected from the groups: alkanediols, alkanetriols, alkanetetraols, carbohydrates, carbohydrates reduced to polyols, oligoalkylene glycols, polyethylene glycols, polypropylene glycols, polybutylene glycols, ethylene oxide-propylene oxide copolymers, polyglycerols;

ethoxylates and propoxylates of alkanediols, alkanetriols, alkanetetraols, carbohydrates, polyols from reduced carbohydrates and of polyglycerols;

amino alcohols, polyglycolamines, ethoxylates and propoxylates of amino alcohols and of polyglycolamines.

Preference is given to using dihydric ether alcohols such as diethylene glycol, triethylene glycol, tetraethylene glycol and polyglycols having an average molar mass between 200 g/mol and 1000 g/mol.

The organic radical R comprises preferably from 1 to 50 and in particular from 2 to 30 carbon atoms. In one preferred embodiment, R comprises O or N or O and N as well as C and H.

The condensation products of the present invention, in addition to the two reactants (A) and (B), may comprise further reactants (C). The further reactant or reactants (C) are selected from the group consisting of water, alkylpolyglycols and silanes of the formula $$SiX_4, R'SiX_3, R'_2SiX_2, R'_3SiX \text{ where}$$

X=Cl or alkoxy in particular methoxy or ethoxy,
R'=alkyl in particular methyl or alkenyl in particular vinyl, or H.

In this case, the reactants (A), (B) and one or more compounds as per (C) are conjointly condensed or polycondensed by detachment of HX. The structure and the properties of these condensation products can be influenced through the choice of (A), (B) and (C), the number of reactive groups in (B) and (C), the mixing ratio of (A), (B) and (C), the order of addition of (A), (B) and (C) and the form of metering and mixing and also the degree of separation of the detached HX from the condensation product. Monohydric alcohols such as alkylpolyglycols reduce the average molar mass and the degree of crosslinking and compounds having 3 or 4 functional groups such as $R'SiX_3$ or $SiX_4$ increase the degree of crosslinking.

The mixing ratios of (A), (B) and if appropriate (C) can be varied within wide limits. Usually (C) is used in smaller proportions than (A) or (B). The condensation or polycondensation reaction is effected by thorough mixing at temperatures at which the resultant condensation products are liquid. In general, the reaction temperatures are between 50° C. and 200° C. in the case of X=Cl and between 100° C. and 250° C. in the case of X=O—$C_nH_{2n+1}$, n=1, 2, 3 or 4. Higher temperatures are also possible when required by the melting range or the viscosity of the condensation product. The reaction can be carried out under superatmospheric pressure, at atmospheric pressure or under reduced pressure. In the case of X=Cl, atmospheric pressure and in particular reduced pressure is preferred to remove the resultant HCl gas rapidly from the reaction mixture. The monohydric alcohol $C_nH_{2n+1}$—OH formed in the course of the condensation reaction when X=O—$C_nH_{2n+1}$ can be distilled out of the reaction mixture continuously or batchwise, completely or else only partially. Depending on (A), (B) and if appropriate (C), the degree of condensation, the molar mass distribution and the degree of crosslinking the condensation products are present at room temperature in liquid, viscid, gellike or solid form.

The condensation products of the present invention are preferably employed in the form of a dilute, generally liquid, formulation. They may be solutions, emulsions or suspensions. Depending on (A), (B) and if appropriate (C), on the molar mass and the degree of branching and crosslinking various solvents or dispersants can be used. Useful solvents or dispersants include for example water or alcohols. Of the alcohols, preference is given to using the alcohols of the formula (B) if they are liquid at room temperature and short-chain, aliphatic, monohydric alcohols, more preferably isopropanol or ethanol. The concentration of the condensation products in the formulations is generally between 0.01% and 30% often preferably between 0.5% and 5%.

As well as the condensation product and one or more solvents or dispersants, the formulations may additionally comprise further components such as neutral, anionic, cationic or amphoteric surfactants, acids, bases and alkoxysilanes. These further components influence the storage stability and shelf life of the formulations, their viscosity and flow behavior on surfaces and also the way surface properties are modified by the respective formulation. Useful surfactants include for example alcohol ethoxylates, alcohol alkoxylates, ethylene oxide-propylene oxide polymers, amine oxides, alkyl sulfates, alkyl ether sulfates, alkylaryl ether sulfates, alkanesulfonates, olefinsulfonates, alkyl polyglycol ether phosphates, quaternary ammonium compounds and betaines. The pH can be set using: inorganic acids such as for example sulfuric acid, alkali metal hydrogensulfate; organic acids such as for example formic acid, acetic acid, propionic acid, citric acid and also inorganic bases such as for example sodium hydroxide, potassium hydroxide, alkali metal carbonate, alkali metal bicarbonate and organic bases such as for example amines or alkali metal acetate. By way of alkoxysilanes, it may be preferable to add tetraalkoxysilanes, in particular tetraethoxysilanes, as a formulation component.

To produce the formulations, the condensation products are dissolved or suspended at room temperature or at elevated temperature, in general below 100° C., in solvents or dispersants, if appropriate in the presence of further auxiliary materials, with stirring. Auxiliary materials refers in particular to neutral, anionic, cationic or amphoteric surfactants, alkoxysilanes such as for example tetraethoxysilane and also acids and bases.

The condensation products of the present invention and their formulations can be applied to surfaces composed for example of glass, ceramic, mineral building materials, lacquers, metal, plastic, wood, paper or textile fabrics. Postcondensation and formation of a firmly adhering, thin surface layer takes place at room temperature or at elevated temperatures which, depending on the identity of the surface, may be up to about 300° C. Similarly, small particles of the order of μm or nm can be coated therewith. These surface coatings endow the surfaces finished therewith with hydrophobic, oleophobic, soil- and ink paint-repelling properties, depending on the application conditions.

The examples which follow illustrate the invention.

EXAMPLE 1

118.3 g (0.788 mol) of triethylene glycol having a water content below 0.1% were placed as initial charge in a 250 ml round-bottom glass flask equipped with magnetic stirring bar, thermometer, dropping funnel with dip tube, nitrogen connection, vacuum connection and heatable oil bath, and were dewatered at 80° C. and about 20 mbar by passing in dry nitrogen and stirring. The introduction of nitrogen was terminated thereafter and the flask contents were heated up to 150° C. 31.7 g (0.0658 mol) of perfluorohexylethyltrichlorosilane of the formula $C_6F_{13}$—$CH_2$—$CH_2$—$SiCl_3$ were added dropwise gradually and continuously within 1.5 hours via the dropping funnel at 150° C. and 20-50 mbar pressure with intensive stirring. The HCl gas which formed in the process was immediately removed via the vacuum system. Following the dropwise addition of the perfluorohexylethyltrichlorosilane, dry nitrogen was bubbled into the clear, liquid reaction product for an hour at 150° C. and about 50 mbar pressure with stirring while residual quantities of HCl were expelled. The condensation product became colorless and liquid at room temperature. The molar mass determined by GPC in THF as mobile phase (molar mass standard: PEG) was about 700 g/mol. $^1$H NMR and $^{29}$Si NMR confirmed the following structure for the reaction product (main components):

$C_6F_{13}$—$CH_2$—$CH_2$—$Si(O$—$CH_2$—$CH_2$—$O$—$CH_2$—$CH_2$—$O$—$CH_2$—$CH_2$—$OH)_3$ dissolved in excess triethylene glycol.

EXAMPLE 2

72.5 g (0.483 mol) of triethylene glycol having a water content below 0.1% were placed as initial charge in a 250 ml round-bottom glass flask equipped with magnetic stirring bar, thermometer, dropping funnel with dip tube, nitrogen connection, vacuum connection and heatable oil bath, and were dewatered at 80-100° C. and about 20 mbar by passing in dry nitrogen and stirring. The introduction of nitrogen was terminated thereafter and the flask contents were heated up to 150° C. 77.5 g (0.161 mol) of perfluorohexylethyltrichlorosilane of the formula $C_6F_{13}$—$CH_2$—$CH_2$—$SiCl_3$ were added dropwise gradually and continuously within 2 hours via the dropping funnel at 150° C. and 20-50 mbar pressure with intensive stirring. The HCl gas which formed in the process was immediately removed via the vacuum system. Following the dropwise addition of the perfluorohexylethyltrichlorosilane, dry nitrogen was bubbled into the clear, liquid reaction product for an hour at 150° C. and about 50 mbar pressure with stirring while residual quantities of HCl were expelled. The condensation product became colorless and viscid at room temperature. The molar mass range determined by GPC in THF as mobile phase (molar mass standard: PEG) was between about 700 and 30 000 g/mol. The end product is according to these GPC findings and NMR data a mixture of monomeric, oligomeric and polymeric condensation products and also small fractions of free triethylene glycol.

EXAMPLES 3 TO 7

Example 1 was repeated with other alcohols and other quantities. The reaction conditions and the procedure in Example 3-7 corresponded to those of Example 1.

| Example | introduced as initial charge | added dropwise | Appearance of Condensation product at 20° C. | Molar mass range by GPC in THF (molar mass standard: PEG) |
|---|---|---|---|---|
| 3 | 97.5 g (0.325 mol) of polyethylene glycol 300 | 52.5 g (0.109 mol) of $C_6F_{13}$—$CH_2$—$CH_2$—$SiCl_3$ | colorless, viscid | 600-26 000 g/mol |
| 4 | 118.2 g (0.394 mol) of polyethylene glycol 300 | 31.8 g (0.0660 mol) of $C_6F_{13}$—$CH_2$—$CH_2$—$SiCl_3$ | colorless, viscid | 600-7000 g/mol |
| 5 | 132.2 g (0.441 mol) of polyethylene glycol 300 | 17.8 g (0.0370 mol) of $C_6F_{13}$—$CH_2$—$CH_2$—$SiCl_3$ | colorless, liquid | 700-2800 g/mol |
| 6 | 107.0 g (0.260 mol) of polyethylene glycol 400 | 43.0 g (0.0893 mol) of $C_6F_{13}$—$CH_2$—$CH_2$—$SiCl_3$ | colorless, viscid | 1300-25 000 g/mol |
| 7 | 136.3 g (0.341 mol) of polyethylene glycol 400 | 13.7 g (0.0285 mol) of $C_6F_{13}$—$CH_2$—$CH_2$—$SiCl_3$ | colorless, viscid | 700-3700 g/mol |

EXAMPLE 8

105.5 g (0.264 mol) of polyethylene glycol 400 and 1.6 g (0.089 mol) of water were placed as initial charge in a 250 ml round-bottom glass flask equipped with magnetic stirring bar, thermometer, dropping funnel with dip tube, nitrogen connection, vacuum connection and heatable oil bath. 42.9 g (0.0891 mol) of perfluorohexylethyltrichlorosilane of the formula $C_6F_{13}$—$CH_2$—$CH_2$—$SiCl_3$ were added dropwise gradually and continuously within 2 hours via the dropping funnel at 150° C. and about 50 mbar pressure with intensive stirring. The HCl gas which formed in the process was immediately removed via the vacuum system. Following the dropwise addition of the perfluorohexylethyltrichlorosilane, dry nitrogen was bubbled into the liquid reaction product for an hour at 150° C. and about 50 mbar pressure with stirring while residual quantities of HCl were expelled. The condensation product became colorless and viscid at room temperature. The molar mass range determined by GPC in THF as mobile phase (molar mass standard: PEG) was between about 900 and 23 000 g/mol. The end product is according to these GPC findings and NMR data a mixture of monomeric, oligomeric and polymeric condensation products.

EXAMPLE 9

170.2 g (0.288 mol) of perfluoroalkylethyltriethoxysilane 612 of the formula $F(CF_2-CF_2)_n-CH_2-CH_2-Si(O-C_2H_5)_3$ (n=3, 4, 5, 6, 7) and 129.8 g (0.865 mol) of triethylene glycol having a water content below 0.1% were conjointly placed as initial charge in a 500 ml round-bottom glass flask equipped with PTFE vane stirrer, 3 thermometers for measuring internal, distillation and oil temperatures, distillation bridge with graduated receiver, nitrogen connection and heatable oil bath. The initially two-phase reaction mixture was nitrogenated and heated to 190° C. at atmospheric pressure with stirring. The reaction temperature was gradually raised from 190° C. to 220° C. After distillative removal of one mole equivalent of ethanol (13 g) and after distillative removal of two mole equivalents of ethanol (26 g) samples of the liquid, now single-phase condensation product were taken each time from the 500 ml round-bottom glass flask (samples 1 and 2). Ethanol no longer distilled over towards the end of the reaction. Total stirring time was 7.3 hours at 190-220° C. (final sample).

| | Appearance at 20° C. | Molar mass range by GPC in THF (molar mass standard: PEG) |
|---|---|---|
| Sample 1 | liquid, pale yellow | 300-3200 g/mol |
| Sample 2 | liquid, moderately viscous, yellow | 300-4700 g/mol |
| Final sample | viscid, yellow | 300-12 000 g/mol |

According to the NMR findings, monomeric compounds of the formula $F(CF_2-CF_2)_n-CH_2-CH_2-Si(O-C_2H_5)_{3-m}[O-CH_2-CH_2-O-CH_2-CH_2-O-CH_2-CH_2-OH]_m$, m=0, 1, 2 and 3, are present, inter alia. The fraction of compounds where m=3 and also the fraction of oligomeric and polymeric condensation products increases in the order sample 1→sample 2→final sample. Sample 1, sample 2 and final sample are for example soluble in isopropanol, acetone or tetrahydrofuran (THF).

EXAMPLE 10

Example 9 was repeated using glycerol in place of triethylene glycol. The amounts used were 204.4 g (0.346 mol) of perfluoroalkylethyltriethoxysilane 612 of the formula $F(CF_2-CF_2)_n-CH_2-CH_2-Si(O-C_2H_5)_3$ (n=3, 4, 5, 6, 7) and 95.6 g (1.04 mol) of glycerol. The reaction temperature was 190° C. and the total reaction time was 6 hours (final sample).

| | Appearance at 20° C. | Molar mass range of THF-solubles by GPC in THF (molar mass standard: PEG) |
|---|---|---|
| Sample 1 (after distillative removal of 16 g of ethanol) | liquid, biphasic, almost colorless | 300-3200 g/mol* |
| Sample 2 (after distillative removal of 32 g of ethanol) | solid, waxy, white | 600-3200 g/mol* |
| Final sample | solid, waxy, white | 800-3200 g/mol* |

*Only the THF-solubles were measured. Especially the final sample was only partially soluble in THF. The molar mass upper limit is probably distinctly higher.

EXAMPLE 11

31.5 g (0.0617 mol) of perfluorohexylethyltriethoxysilane of the formula $C_6F_{13}-CH_2-CH_2-Si(O-C_2H_5)_3$, 255.7 g (0.639 mol) of polyethylene glycol 400 and 12.8 g (0.0615 mol) of tetraethoxysilane of the formula $Si(O-C_2H_5)_4$ were conjointly placed as initial charge in a 500 ml round-bottom glass flask equipped with PTFE vane stirrer, 3 thermometers for measuring internal, distillation and oil temperatures, distillation bridge with graduated receiver, nitrogen connection and heatable oil bath. The reaction mixture was nitrogenated and heated to 170° C. at atmospheric pressure with stirring. The released ethanol was distilled off. The reaction temperature was gradually raised up to 210° C. The reaction was discontinued after 6.25 hours.

The end product was yellowish and liquid and moderately viscous at 20° C. The molar mass range determined by GPC in THF as mobile phase (molar mass standard: PEG) was between about 900 and 20 000 g/mol. Suitable solvents were isopropanol, water, acetone, THF or polyethylene glycols.

EXAMPLE 12

218.9 g (0.429 mol) of perfluorohexylethyltriethoxysilane of the formula $C_6F_{13}-CH_2-CH_2-Si(O-C_2H_5)_3$ and 81.1 g (1.33 mol) of ethanolamine of the formula $HO-CH_2-CH_2-NH_2$ were placed as initial charge in a 500 ml round-bottom glass flask equipped with PTFE vane stirrer, 3 thermometers for measuring internal, distillation and oil temperatures, distillation bridge with heatable ascending condenser (80° C.), descending condenser and graduated receiver, nitrogen connection and heating mantle with relay. The reaction mixture was nitrogenated and heated under atmospheric pressure to 120° C. with stirring. The released ethanol was distilled off. The reaction temperature was gradually raised up to 200° C. The reaction was discontinued after 6.75 hours.

The end product with the main component of the formula $C_6F_{13}-CH_2-CH_2-Si(O-CH_2-CH_2-NH_2)_3$ ($^1$H NMR and $^{29}$Si NMR) was yellowish and liquid and moderately viscous at 20° C. The compound dissolved for example in isopropanol, tetrahydrofuran or chloroform.

EXAMPLE 13

183.1 g (0.359 mol) of perfluorohexylethyltriethoxysilane of the formula $C_6F_{13}-CH_2-CH_2-Si(O-C_2H_5)_3$ and 116.9 g (1.11 mol) of 2-(2-aminoethoxy)ethanol of the formula $H(O-CH_2-CH_2)_2-NH_2$ were placed as initial charge in a 500 ml round-bottom glass flask equipped with PTFE vane stirrer, 3 thermometers for measuring internal, distillation and oil temperatures, distillation bridge with heatable ascending condenser (80° C.), descending condenser and graduated receiver, nitrogen connection and heating mantle with relay. The reaction mixture was nitrogenated and heated under atmospheric pressure to 125° C. with stirring. The released ethanol was distilled off. The reaction temperature was gradually raised up to 200° C. The reaction was discontinued after 7 hours.

The end product with the main component of the formula $C_6F_{13}$—$CH_2$—$CH_2$—$Si[(O$—$CH_2$—$CH_2)_2$—$NH_2)]_3$ ($^1H$ NMR and $^{29}Si$ NMR) was yellowish and liquid and moderately viscous at 20° C. The compound dissolved for example in isopropanol, tetrahydrofuran or chloroform.

EXAMPLE 14

The table which follows recites formulations obtained by mixing the inventive condensation products of Examples 1 to 13 with solvents, dispersants and further additives such as for example surfactants or additions to adjust the pH.

All the formulation examples recited utilized 1.5 g of the condensation product according to the present invention, which was mixed with the additives by stirring or shaking.

| Formulation No. | Condensation product of example No. | Additive/amount of additive |
|---|---|---|
| 1 | 1 | Water/48.5 g |
| 2 | 1 | Water/48.45 g |
|   |   | Genaminox LA ®/0.05 g |
| 3 | 1 | Isopropanol/48.5 g |
| 4 | 2 | Isopropanol/48.35 g |
|   |   | Sulfuric acid conc./0.15 g |
| 5 | 2 | Isopropanol/45.85 g |
|   |   | Tetraethoxysilane/2.5 g |
|   |   | Sulfuric acid conc./0.15 g |
| 6 | 2 | Triethylene glycol/48.5 g |
| 7 | 3 | Polyethylene glycol 300/48.5 g |
| 8 | 4 | Water/48.45 g |
|   |   | Genaminox LA ®/0.05 g |
| 9 | 8 | Water/48.5 g |
| 10 | 8 | Water/48.45 g |
|    |   | Genaminox LA ®/0.05 g |
| 11 | 8 | Isopropanol 48.5 g |
| 12 | 9/sample 1 | Isopropanol/48.5 g |
| 13 | 9/sample 2 | Isopropanol/48.5 g |
| 14 | 9/final sample | Water/48.5 g |
| 15 | 9/final sample | Water/48.45 g |
|    |   | Genapol LRO liquid ®/0.05 g |
| 16 | 10/sample 2 | Isopropanol/45.85 g |
|    |   | Tetraethoxysilane/2.5 g |
|    |   | Sulfuric acid conc./0.15 g |
| 17 | 10/final sample | Isopropanol/48.5 g |
| 18 | 11 | Water/48.45 g |
|    |    | Genaminox LA ®/0.05 g |
| 19 | 12 | Isopropanol/48.5 g |
| 20 | 12 | Isopropanol/48.35 g |
|    |    | Acetic acid conc./0.15 g |
| 21 | 13 | Isopropanol/48.5 g |
| 22 | 13 | Isopropanol/48.35 g |
|    |    | Acetic acid conc./0.15 g |

Genaminox LA ®: lauryldimethylamine oxide (30% in water)
Genapol LRO liquid ®: $C_{12}/_{14}$ alkyl diglycol ether sulfate, Na salt (27% in water)

The formulations Nos. 1 to 22 were wiped with a polyamide cloth onto glass microscope slides previously cleaned with isopropanol. After one day at room temperature, the glass surfaces coated with the formulations were compared with an uncoated glass surface with regard to behavior in relation to water droplets. The high, spherical shape of the water droplets and the improved flow-off behavior showed that the formulations Nos. 1 to 22 had conferred enhanced hydrophobic properties on the glass surfaces.

I claim:

1. A compound prepared by reacting fluorous silanes (A)

$$R_F\text{—}CH_2\text{—}CH_2\text{—}SiX_3 \quad (A)$$

where
  $R_F$ is a fully or partially fluorinated alkyl radical,
  X is Cl or O—$C_nH_{2n+1}$, and
  n is an integer from 1 to 20,
with one or more alcohol of the formula (B)

$$R(OH)_m(NH_2)_p \quad (B)$$

where
  R is an organic radical comprising C, H and O atoms and m and p are subject either to condition
  a) $m \geq 2$ and $p=0$, or condition
  b) $m \geq 1$ and $p \geq 1$.

2. The compound of claim 1 wherein $R_F$ is a radical of the formula (1)

$$R_F'\text{—}(CH_2\text{—}CF_2)_b\text{—} \quad (1)$$

where $R_F'$ is a perfluoroalkyl group having 1 to 16 carbon atoms and b is an integer from 1 to 12.

3. The compound of claim 1 wherein $R_F$ is a radical of the formula (2)

$$F\text{—}(CF_2\text{—}CF_2)_d\text{—} \quad (2)$$

where d is an integer from 1 to 12.

4. The compound of claim 1, wherein the alcohol is selected from the group consisting of alkanediols, alkanetriols, alkanetetraols, carbohydrates, carbohydrates reduced to polyols, oligoalkylene glycols, polyethylene glycols, polypropylene glycols, polybutylene glycols, ethylene oxide-propylene oxide copolymers, polyglycerols; ethoxylates and propoxylates of alkanediols, alkanetriols, alkanetetraols, polyols from reduced carbohydrates and of polyglycerols; amino alcohols, polyglycolamlnes. ethoxylates and propoxylates of amino alcohols and, of polygiycolamines, and mixtures thereof.

5. The compound of claim 1, wherein the alcohol is selected from the group consisting of diethylene glycol, triethylene glycol, tetraethylene glycol, polyglycols having, an average molar mass between 200 g/mol and 1000 g/mol, and mixtures thereof.

6. The compound of claim 1, further comprising reacting one or more further reactant (C) being conjointly condensed or polycondensed, wherein the reactant (C) is selected from the group consisting of water, alkylpolyglycols, silanes of the formula $SiX_4$, $R'SiX_3$, $R'_2SiX_2$, $R'_3SiX$ where
  X=Cl or alkoxy
  R'=alkyl, alkenyl, or H,
and mixtures thereof.

7. A formulation comprising the compound of claim 1 and one or more further component selected from the group consisting of
  (a) a solvent,
  (b) water,
  (c) a surfactant selected from the group consisting of a neutral, anionic, cationic, and amphoteric surfactant,
  (d) an alkoxysilane,
  (e) an acid,
  (f) a base, and mixtures thereof.

8. A method for modifying the properties of surfaces and small particles, said method comprising coating said surfaces and small particles with a coating comprising the compound of claim 1.

9. A method for hydrophobicizing and oleophobicizing a surface, said method comprising applying a coating comprising the compound of claim 1 to said surface, said surface selected from the group consisting of glass, ceramic, mineral building materials, lacquers, metal, plastic, wood, paper, and textile fabrics.

10. The method of claim 8, wherein said small particles are from about 1 μm to about 1 nm.

11. The formulation of claim 7, wherein the solvent is an alcohol.

12. The formulation of claim 11 wherein the alcohol is isopropanol.

13. The formulation of claim 7, wherein the alkoxysilanes are alcohols.

14. The method of claim 8 wherein said surface properties are selected from the group consisting of hydrophobic, oleophobic, soil-repelling, ink-repelling, paint-repelling, and combinations thereof.

15. The method of claim 9, wherein said surface comprises small particles of from about 1 μm to about 1 nm.

* * * * *